United States Patent [19]

Manzatu et al.

[11] Patent Number: 5,965,151
[45] Date of Patent: Oct. 12, 1999

[54] BIOACTIVE CONCENTRATE, ITS PRODUCING METHOD AND CERTAIN DRUG COMPOSITIONS CONTAINING ALSO CHONDROITIN SULPHATE

[75] Inventors: Ioan Manzatu; Dan-Etienne Arizan; Vasile Ionita-Manzatu; Marian Carasava, all of Bucharest; Maria Panait, Constanta; Irina-Gabriela Scarlat, Bucharest, all of Romania

[73] Assignee: S. C. Tehman S.R.L., Bucharest, Romania

[21] Appl. No.: 08/930,956

[22] PCT Filed: Mar. 14, 1996

[86] PCT No.: PCT/RO96/00003

§ 371 Date: Oct. 3, 1997

§ 102(e) Date: Oct. 3, 1997

[87] PCT Pub. No.: WO96/32117

PCT Pub. Date: Oct. 19, 1996

[30] Foreign Application Priority Data

Apr. 11, 1995 [RO] Romania ................... 9500699

[51] Int. Cl.$^6$ .................. A61F 2/02; A61F 13/02
[52] U.S. Cl. ............. 424/423; 424/433; 424/443; 424/DIG. 15
[58] Field of Search ................. 424/422, 423, 424/433, 443, DIG. 15

[56] References Cited

U.S. PATENT DOCUMENTS 4,411,988  10/1983  Toth et al. ................... 435/7

FOREIGN PATENT DOCUMENTS 82273  8/1983  Romania.

*Primary Examiner*—Carlos A. Azpuru
*Attorney, Agent, or Firm*—Herbert Dubno

[57] ABSTRACT

This bioactive concentrate is an active substance—aqueous solution or lyophilized powder—consisting of antihyaluronidase and antiinflammatory mucopolysaccharide polymers and an addition of restitutive and antihyaluronidase chondroitinsulphate, which has a pH=4–6 and antihyaluronidase activity. The bioactive concentrate producing method consists in a two—phased treatment of animal—originated connective cartilaginous tissues such as bovine and sheep trachea, umbilical cord, young animal tendons, bowels, testicles or sea organisms, with phenol solution and the solution resulted is concentrated by vacuum evaporation and then defatted; after filtering, the supernatant obtained is treated for deproteinization, the ion excess is removed by passing through ion exchanger column, the alcohol solution is concentrated to remove alcohol until reaching a volume of 70% as against the aqueous solution subject to proteinzation. Drug compsitions contain the bioactive concentrate—solution or in lyophilized state— associated with synergic substances such as: heparin, sodium or lysin acetylsallicylate, ascorbic acid, vitamin E,"I"-like structured water, benzyl alcohol, propylene glycocou, plant extracts (Achillea, Calendula, Matricaria, Plantago, Hypericum) and usual excipients, being conditioned in the form of intramuscular or intraarticular injections, ointment, gel and suppositories. Finally the histamines are removed and chondroitin sulphate is added up to the concentration required.

18 Claims, No Drawings

BIOACTIVE CONCENTRATE, ITS PRODUCING METHOD AND CERTAIN DRUG COMPOSITIONS CONTAINING ALSO CHONDROITIN SULPHATE

FIELD OF THE INVENTION

This invention relates to a bioactive concentrate, a method of producing same and pharmaceutical compositions containing the bioactive concentrate for treatment of degenerative diseases, including rheumatism, arthropaties and other related diseases.

BACKGROUND OF THE INVENTION

A complex of anti-hyaluronidase substances has been derived from several natural products, such as small fish containing amino acids, whole glucides, glycogen chondroitinsulphate, phenol, hypotensive substances, with an antihyaluronidase activity of a minimum of 50 I.U/ml.

The method whereby the complex is produced consists of a two-phased treatment of se fish with 0.5% phenol solution, over a period of 24 h, the extracts brought together are vacuum concentrated at a maximum 40° C., then they are treated with an equal ethanol $96^c$ volume; the precipitate is removed and the supernatant obtained is treated with celite, filtered, vacuum-concentrated at a maximum 40° C., then solvent-extracted—treated and after removing the solvent the supernatant is treated with phenol up to a value of 4.5–5.5%.

Drug compositions containing an anti-hyaluronidase bioactive extract, phenol and sodium metabisulphite, have been developed too.

These drugs rely on a complex of substances, natural active principles, associated in proportions close to the normal, functional ones, produced by extraction from animal tissues or biosynthesized in cells and microorganism cultures, the role of this complex being to replace, to substitute for or even to allow recovery of the naturally existing complex in connective tissues, that had been unbalanced for various reasons and which caused the disease.

The extraction and conditioning processes have been established so that losses and degradation of active substances should be as low as possible and when the ratio of raw material constituents is different from that one required to treat disease in human being, it may be set off by a proper compounding of extracts or by a treatment schedule.

Now, the disease-inducing mechanisms are known to result from a disequilibrium in the biosynthesis and breakdown of normal constituents on which the proper movement of joints depends.

Cells in the tissues of the living body are embedded and evolve within basic substances. This basic substance—a general compound of living structures-pervades every interspace and isolates every stationary cell from its neighbors. Variations in the composition of the extracellular environment exert a profound influence on cell behavior and in turn the cells possess a powerful means of modifying their immediate environment.

The intercellular substance is a complex gel containing water, electrolytes, metabolites, dissolved gases, enzymes, trace elements, fats, proteins, carbohydrates. This substance is rendered highly viscous by an abundance of certain long-chain acid mucopolysaccharide polymers, particularly glycosaminoglycans and the related proteoglycans, reinforced at the microscopic level by a three-dimensional network of collagen fibrils (Cameron, E. and Pauling, L—The Encyclopedia of Ignorance, p. 377–385, Pergamon Press, Oxford, 1982).

The role of synovial fluid, found in all joints, is not only to lubricate the moving structures but also to dissipate the energy.

This function is performed by the synovial fluid composition where the glycosaminoglycans (GAC) and proteoglycans (PG such as hyaluronic acid and chondroitinsulphate inducing a high viscosity with their spiral structure, behave viscous-like when the moving frequencies are low and elastic—like when the moving frequencies are high (Ogston, A. G. and Stanier, J. E. (1953)—J. Physiol, 199, 124).

Elasticity is due to the presence of the highly concentrated hyaluronic acid, at a pH=2.5 which forms a viscous-elastic paste in a salt solution (Balasz, E. A., Chemistry and Molecular Biology of the Intercellular Matrix, Vol. II and III, Academic Press, New York, 1970).

At different ages, the synovial fluid behaves similarly as it concerns viscosity, but the energy taking over is different at high moving frequencies, the synovial fluid in young people taking over 77% of the energy while in the old it takes over only 52% of the energy by elastic storage.

The synovial fluid in affected joints (osteoarthrosis) is viscous, but not elastic. The stiffness of this synovial fluid is 7 times lower than that one in the healthy old people. The hyaluronic acid concentration in these fluids is low, resulting in low viscosity indices and the protein concentration is high. The negative influence of concentration change may lower in some cases, the viscosity index up to 30 times.

Also, in joints, tendons, vitreous bodies of the eye—the fluid area (synovial fluid, vitreous fluid) is adjacent to the solid matrix (articular cartilage, tendon, fascia, vitreous body).

The viscous-elastic macromolecular compound—the hyaluronic acid—in the fluid matrix, penetrate the solid matrix surface. Rheologically, the major difference between the two matrices is the presence of collagen fibrils in the solid matrix and their absence in the fluid one.

The surface layer of $1-2\mu$ consists of hyaluronic acid and proteins. This layer can be removed or destroyed by the action of hyaluronidase, found in excess in the intercellular matrix.

The sublayer of $10-15\mu$ in thickness contains typical collagen fibrils, and the interfibrillar space is filled with approximately equal amount of hyaluronic acid and chondroitinsulphate. on the basis of the data known from the specialized field (Cameron, E. and Pauling, L—The Encyclopedia of Ignorance, p. 377–385, Pergamon Press, Oxford, 1982 and Balasz, E. A. and Sweeney, D. B.—11968—New and Controversial Aspects of Retinal Detachment, p. 371, Ed. McPerson, Harpen and Row, N.Y.), this invention aimed at producing a complex of ingredients in which the mucopolysaccharide polymers and proteoglycans take part under the form of hyaluronic acid and chondroitinsulphate, as well as their fragments, herparin and ascorbic acid, all of them being substances certified by recent investigations, contributing to restore the normal functions in the connective tissues, in the case of degenerative diseases. These diseases, altering the basic substance in which the cells are embedded, deteriorates the relationship existing between the basic substance and these cells. The condition for a "normal" balance is for each part—the basic substance and the cell—to keep its own functions, since any change, as for instance the reduction in basic substance viscosity by hyaluronic acid depolymerizing through the action of hyaluronidase secreted in excess by cells, is followed by disease occurrence.

Another alternative to restore the balance is the association of an antienzyme called anti-hyaluronidase (hyaluronidase is after all, an enzyme group with the same functions as the connective structures), that stops or limits the hyaluronic acid depolymerization, alongside chondroitinsulphate, heparin and ascorbic acid.

Some attempts have been already known, to prepare drugs based on anti-hyaluronidase which is extracted from its containing sources, such as: bovine trachea, bovine and sheep testicles, umbilical cord, small sea fish, etc.

Although important at that time (Patent RO/82273-1982 and Technological Reports drawn up by the Institute of Chemical and Pharmaceutical Research-Bucharest, No. 84740/1977 and No. 5160/1979), these attempts represented an elementary alternative solving only partially the question of both producing method and the composition of the drugs achieved.

SUMMARY OF THE INVENTION

According to this invention, the bioactive concentrate is an active substance—10% aqueous solution consisting of 7–9% anti-hyaluronidase and antiinflammatory mucopolysaccharide polymers and an addition of up to 1–3% restitutive and anti-hyaluronidase chondroitinsulphate, which has a pH=4–6 and an anti-hyaluronidase activity of 450–750 I.U./ml. This concentrate is yellowish to light brown; in a lyophilized state and contains at lest 93% active substance consisting of 65–84% mucopolysaccharide polymers and 9–28% chondroitinsulphate, and contains usual preservatives. The method of producing the bioactive concentrate consists in the two-phased treatment of animal-originated cartilaginous connective tissues such as bovine and sheep trachea, umbilical cord, young animal tendons, bowels, testicles or sea organisms, with an acid aqueous solution containing 0.5% phenol, pH=2–4, in the first phase in a ratio of 1:3.5–4 and in the second phase in a ratio of 1:1.5, in both phases the extraction takes a period of 24 h, stirring for 30 minutes every 3 h, at a temperature between 0–4° C., and then the extract obtained in the first phase is combined with that one resulted from the second phase and adjusted to a pH=4.5–5 with Ca (OH)$_2$ solution. The combined extracts are allowed to settle at 0–4° C. for 8 hours, then filtered and the solution obtained is concentrated by vacuum evaporation at a maximum temperature of 45° C. until a concentration ratio of 7:1 is obtained. Thereafter the solution is passed through an ion-weak anion exchanger column and afterwards the solution is defatted by solvent extraction in a ratio of 1:4 in 6–10 cycles until the remanent lipids should not exceed 1–5%. The last defatting cycle is performed with n-hexane in the same ratio; then the resulting aqueous solution is vacuum concentrated until reaching a volume of 70% of the original solution. After filtering, the supernatant obtained is treated with 96° ethanol for deproteinization until reaching an ethanol concentration of 50%, then left in a cool place at 0–5° C. for 12 h. Afterwards the supernatant is filtered and the ethanol solution concentrated to remove the alcohol until reaching a volume of 70%. As against the aqueous solution subject to deproteinization, the protein precipitate is gradient—treated with ammonium sulphate and the low molecular weight protein fraction is combined with the aqueous solution from where the alcohol and the histaminic impurities were removed by successively treating of the final solution with trisodium phosphate until reaching a pH=8.5. Then the solution is filtered and the solution obtained is passed through an ion-weak cation exchanger column—pH value reverts to 4–6 and then chondroitinsulphate is added in a concentration of 1–3%. The raw material can be in the fresh, frozen or preserved state. Passage of the solution through weak cationic exchange resins is performed at a flow not exceeding, per hour, ⅕ of the original solution volume.

Drug compositions contain the bioactive concentrate—solution or in lyophilized state, associated with synergists such as: heparin, sodium or lysin acetylsallicylate, ascorbic acid, vitamin E, "I"-like structured water, benzyl alcohol, propylene glycol, plant extracts (Achillea, Calendula, Matricaria, Plantago, Hypericum) and usual excipients being conditioned in the form of intramuscular injections, intraarticular injections, ointments, gels and suppositories.

For intramuscular administration, the composition includes in 1 ml of aqueous solution, 0.1 ml bioactive concentrate solution 10% or 11 mg lyophilized bioactive concentrate, maximum 5 mg phenol and 2 mg sodium metabisulphite, has a pH=4.6 and an anti-hyaluronidase activity of minimum 45 I.U./ml. For intraarticular administration, the composition includes, in 1 ml of aqueous solution, 15 mg/ml dry active substance consisting of bioactive concentrate solution 10% or 16.5 mg lyophilized bioactive concentrate, 10 mg sodium or lysine acetylsallicylate, 2 mg ascorbic acid, 0.2 mg heparin, 20 mg benzyl alcohol, 40 mg propylene glycol has a pH=4–6, an antihyaluronidase activity of minimum 65 I.U/ml and the administering dose is 2 ml; other types of preservatives can be used too, such as 2 mg sodium metabisulphite, 5 mg phenol, provided that the properties of active substances or the final product quality should not be altered. For conditioning in the form of ointment, gel or suppositories, the composition includes, in 100 g, 3–10 g dry substance consisting of the bioactive concentrate solution 10% or 4–12 g lyophilized bioactive concentrate, 0.3–0.5 g sodium or lysine acetylsallicylate, 0.2–0.4 g Vitamin E, 0.4–0.8 g ascorbic acid preferably 0.5 g, 0.2 g heparin, 2–5 g plant whole extract, emulsified in a cream or gel base containing 40–75 g "I"-like structured water, preferably 65 g, usual preservatives and flavorants. Plants used can be: Achillea millefolium, Calendula Officinali, Matricaria Chamomilla, Plantago sp, Hypericum Perforatum. "I"-like structurated water is a water having an enhanced energetic potential, a high transmembrane penetrating capacity and a profound antiinflammatory and antiinfectious effect (Patent RO No. 109835 B.1/1995, authors: Manzatu Ioan and Ionita-Manzatu Vasile).

The solution proposed in this invention solves some of the drawbacks found in the cited works, since this is a key process, achieving a highly efficient extraction of anti-hyaluronidase alongside chondroitinsulphate, in a ratio similar to the existing one in the ground substance, therefore in joints too.

If the raw material wherefrom the extraction is made lacks the needed proportion of chondroitinsulphate, then to the final product chondroitinsulphate obtained from other raw material is added by a process of intensive utilization.

In this way, the following drugs are achieved: injectable solution as such or consisting of lyophilized powder for intramuscular administration, injectable solution as such or consisting of lyophilized powder for intraarticular administration, an ointment and gel for external, local use and suppositories for anal administration.

These drugs are used according to a treatment schedule that allows some synergistic effects to be obtained, which result in enhancing the action of each constituent individually.

By its action, the bioactive concentrate prevents disorganization of the normally—constituted macromolecular structure and stimulates the tissue and periarticular restructuring processes in inflammatory diseases at interstitial and periarticular level, as well as at the particular cartilage level, positively influences the calcium ion dynamics in antiinflammatory, regenerative, biostimulative, demo-and tissue-testitutive effects and stimulates the metabolism of convalescent patients.

All the five drug compositions treat the cause of the disease by restoring the cellular and intercellular mechanisms at the same time as stopping the hyaluronidase excess and starting the tissue recovery process. The compositions are easy to administrate and have no side effects.

The method of producing the bioactive concentrate can be used on an industrial scale, with low energy consumption and recovery of substances used.

The extraction process proposed, besides the fact that it is highly efficient, in the first phase, at a pH=2–4, eliminates many drawbacks found, since selective purifying phases are included, such as histamine removal, a required operation since some batches of previous products had inadequate results for histamine test, leading to their throwing away because of their hypotensive effects. Also ion exchanger deionization was included to reduce the high ion load following repeated concentration operations.

In the end, the most important process included in the extraction flow the achievement of a parallel extraction flow for refuse recovery, thus a higher content of amino acids and chondroitinsulphate being provided, which has not occurred in the previously cited works.

Ultimately, the addition of heparin and ascorbic acid makes it possible to also achieve an injectable solution, intended to intraarticular use as well as the appropriate ointment, gel and suppositories.

BEST MODE OF CARRYING OUT THE INVENTION

Four examples of the invention accomplishment are given below:

EXAMPLE 1

To achieve bioactive concentrate, the raw material subject to the extraction process consists of both the animal—originated cartilaginous, connective tissues—bovine and sheep trachea, umbilical cord, young animal tendons—and bowels, testicles or small sea fish. The raw material is the one to start with, that is small sea fish (anchovy), in an amount of 20 kg. in a fresh, frozen or preserved and desalted state, which after defreezing or desalting is chopped in sizes of 2–6 mm and the extraction is made at a temperature of 3–5° C., with 75 l aqueous solution containing 0.5% phenol and having a pH=2 to 4.

The pH value is adjusted using N (normal) HCl solution, in the phenol solution, before adding chopped raw material.

The first extraction is made in suitable glass or enamelled cast iron tanks, intermittently stirring at 90–120 rot./min. for 30 minutes, to stir every 3 hours, for 24 hours. The solution obtained is separated by centrifugation using as filtering material a fabric of more than 100 stitches/cm$^2$ and in the second extraction, with 30 l phenol solution 0.5% with a pH-2–4 adjusted like above and the operation takes another 24 hours, stirring intermittently too.

The extracts I and II are combined and filtered using craped paper (industrial filter) and the sea paste is a refuse.

The solution extracted and filtered in this way is adjusted to a pH=5 using Ca (OH)$_2$ solution, being then allowed to settle for 8 hours, at a temperature of 0–4° C.

Filtering is repeated with an industrial filter in order to remove the precipitate and implicitly the chlorine ion surplus.

The filtrate, in a volume of about 95 l, is concentrated by vacuum evaporation at an internal temperature of maximum 45° C. The concentration ratio is 7:1, thus 13.5 l of a brownish—yellow suspension concentrate are obtained.

After concentrating, the pH value is controlled, which ranges between 4–6 and some of the ions are removed by passing the filtrate through a weak anion exchanger column.

The solution is passed through the ion exchanger column at a rate of about 2 l/h so that upon leaving the column the solution should have a pH=4–6.

This resultant solution is defatted by solvent extraction, in repeated cycles, using 3 l solvent for each passage, the duration of stirring and resting process being 2 hours. This process is repeated 6–10 times and the efficiency is controlled so that finally, the residual lipids should not exceed 1–5%.

The extracted lipid in the extraction solvent is separated by settling, in suitable containers and then it is distilled for solvent recovery in a ratio of 70–75%. Defatting can also be made with dichlorethane, ethylene trichloride or n-hexane. It is preferably for the last defatting cycle to be made with n-hexane using about 3 kg of this solvent.

The defatted aqueous solution is vacuum concentrated, to about 9 l to remove the solvent traces.

The supernatant is filtered with an industrial paper filter, to remove the precipitate formed during concentration and then it is treated with ethyl alcohol, for deproteinization.

In the filtered supernatant solution 96° ethyl alcohol is added, finely jetting under stirring until an alcohol concentration of 50% is reached. Then it is left in a cool place at 0–5° C. for 12 hours. The precipitate formed is filtercentrifugated through a fabric of minimum 100 stitches/cm$^2$, at 3,000 rot./min.

The residue found on the centrifuge filter is washed using about 3 l alcohol solution 50%. The alcohol solutions obtained in this way are combined and vacuum concentrated to recover the alcohol. About 7 l aqueous solution containing antihyaluronidase active ingredients is finally achieved.

The protein precipitate, achieved in the defatting phase is fractioned with ammonium sulphate and the low molecule proteic fractions resulted from the first phase of deproteinization are combined with the concentrated solution resulting from the first phase of deproteinization. This solution is purified to be free of histaminic impurities, is treated with 350 g trisodium phosphate, 200 g calcium chloride and about 300 ml sodium hydroxide solution 20%. The trisodium phosphate and calcium chloride are added in the form of aqueous solution 30%. The sodium hydroxide solution is added to adjust the pH value to 8.5 and it is left for 24 hours at 0–5° C., then it is filter-centrifugated through a fabric of 100 stitches/cm$^2$ and the solution is retained. The about 9 l of the solution obtained in this way are passed through an ion-weak cationic exchanger, which are regenerated using 0.5% sodium hydroxide solution. The ion exchanger column is treated with 0.5% phenolate water before solution passage. The operation is repeated until reaching the admissible degree of histaminic test.

The resulted solution is filtered. Chondroitinsulphate is added up, if necessary to reach a concentration of 1–3%. About 9 l concentrated solution of about 10% active substance, with a pH-4–6 is achieved.

The concentrated solution is analyzed, the dry substance and hyaluronidase activity are determined.

Five drugs can be produced from this concentrated solution or lyophilized powder by dilution with distilled, apyrogenic water, namely injectable solution for intramuscular administration, injectable solution for intraarticular administration, ointment or gel for local application or suppositories.

EXAMPLE 2

The drug composition for intramuscular administration is achieved by diluting the concentrated solution or lyophilized powder with apyrogenic water, containing maximum 5 mg/ml phenol and maximum 2 mg/ml sodium metabisulphite. The dilution ratio is established so that the injectable solution should contain, in 1 ml aqueous solution, 0.1 ml bioactive concentrate solution 10% or 11 mg lyophilized bioactive concentrate and have an antihyaluronidase activity of minimum 45 I.U./ml.

The solution is first filtered through filters with a porosity of $0.45\mu$ for clarification and then through filters of $0.22\mu$ for sterilization.

They are aseptically packed into brown vials of 1 ml. These standard vials of 1 ml contain: 10 mg/ml active substance, consisting of 7–9 mg antihyaluronidase and anti-inflammatory mucopolysaccharide polymers and prevalently reconstitutive chondroitinsulphate added up to 1–3 mg. usual preservatives and it has a pH-4.6.

If the lyophilized bioactive concentrate is used, in vials of 10 ml containing 110 mg lyophilized bioactive concentrate and a proper preservative up to 25 mg. this vial is equivalent to 10 standard vials, after dissolving in distilled water.

EXAMPLE 3

The drug composition for intraarticular administration is obtained by diluting the concentrated solution or lyophilized powder with apyrogenic water, which contains 20 mg/ml benzyl alcohol and 40 mg/ml propylene glycol (Rote Liste—1993, Publishing House Cantor Aulendort/Wurttemberg, Germany). As active synergistic substances 10 mg/ml sodium or lysine acelylsallicylate, 2 mg/ml ascorbic acid and 0.2 mg/ml heparin are added.

The dilution ratio of the concentrated solution or lyophilized powder is established so that the injectable solution should have a concentration of 1.5% active substance and an anti-hyaluronidase activity of minimum 65 I.U./ml.

The solution intended to be packed into vials is first filtered through filters with a porosity of $0.45\mu$ for clarification, and then through filters of $0.22\mu$ for sterilization and thereafter it is aseptically packed into brown vials of 2 ml.

These vials contain 15 mg/ml active substance consisting of 10–13 mg/ml anti-hyaluronidase and antiinflammatory mucopolysaccharide polymers, reconstitutive chondroitinsulphate up to 2–5 mg/ml, 2 mg/ml ascorbic acid and 0.2 mg/ml heparin at a pH=4–6.

Another conditioning may be performed using 0.5% aqueous phenol solution and 0.2% sodium metabisulphite.

EXAMPLE 4

The drug composition for external, local administration ointment, gel or suppositories—is achieved in a base of—ointments, gel or suppositories, at 100 g: 3–10 g dry active substance consisting of 10% bioactive concentrate solution or 4–12 g lyophilized bioactive concentrate, containing 7–9 anti-hyaluronidase and anti-inflammatory mucopolysaccharide polymers, chondroitinsulfate added up to 1–3 g, 0.4 g vitamin E, 0.5 g ascorbic acid, 0.5 g sodium or lysine acetylsallicylate, 0.2 g heparin, 2–5 g plant whole extracts (Achillea millefolium, Calendula officinalis, Matricaria chamomilla, Plantago sp., Hypericum Perforatum). It is worth mentioning that the base of ointment, gel or suppositories is prepared using 60–75% "I"-like structured water. The ointment base also contains usual preservatives and flavorants. The "I"-like structured water is the object of the Patent No. RO 109835 B, and it is a water of an enhanced energetic potential, a high transmembrane penetrating capacity and a profound anti-inflammatory and antinfectious action. This water is achieved by passing the filtered tap water through activating electromagnetic fields.

The structured water of the "I" type inhibitively activated has been obtained from filtered tap water added to a chemically neutral, parallelopipedic column, with several structuring cells, each one made of a pair of activators, each of them having two lamellar electrodes, one negative and the other one positive, made of stainless net, placed on one and the other side of two chemically inert porous membranes. Following the interaction processes of the water dipolar molecular structures and the electrostatic field that occurred between the two electrodes, in the "I" water-producing spaces, a process occurs by which there are provided arrangements, polarizations and the energy needed to bind the water molecules, by hydrogen bonds, in polymolecular aggregates having negative radicals R', resulting in "I" structured water with a pH between 1.8 and 3 and conductivity between 900 to 3000 $\mu$S/cm, which is disposed from the left-hand and right hand spaces respectively, of the positive electrodes of each activator.

We claim:

1. A bioactive concentrate in a 10% aqueous solution comprising as active principle 7% to 9% of an anti-hyaluronidase and anti-inflammatory mucopolysaccharide polymer and 1% to 3% of chondroitin sulfate, all of these being said active principle having a yellow to light brown color, a pH value ranging from 4 to 6, and an antihyaluronidase activity ranging between 450 and 750 I.U./ml, said bioactive concentrate prepared by a process which comprises the steps of:

(a) extracting at a temperature of 0 to 4 degrees centigrade an organic raw material selected from the group consisting of bovine or sheep cartilaginous connective tissue, umbilical cord, young animal tendons, bowels, and testicles, and sea animals with an aqueous acid solution that contains 0.5% phenol and which has a pH of 2 to 4, in a first phase in a ratio of 1:3.5 to 4 of raw organic material to aqueous acid solution to obtain a first extract and in a second phase in a ratio of 1:1.5 of raw organic material to aqueous acid solution to obtain a second extract, said first phase and said second phase each taking place for 24 hours, stirring for 30 minutes every 3 hours;

(b) combining the first extract and the second extract to obtain a combined aqueous extract;

(c) adjusting the pH of the combined aqueous extract to 4.5 to 5 with calcium hydroxide solution, being then allowed to settle for 8 hours at a temperature of 0 to 4 degrees centigrade;

(d) filtering the combined aqueous extract and concentrating the filtrate by vacuum evaporation at an internal temperature of up to 45 degrees centigrade until reaching a rate of concentration of 7:1;

(e) passing the combined aqueous extract concentrated during step (d) through an anion exchanger column to obtain an aqueous solution;

(f) removing lipids from the aqueous solution by solvent extraction in a ratio of 1:4 solution to extraction solvent in 6 to 10 cycles until the lipids remaining in the aqueous solution do not exceed 1% to 5%, the last defatting cycle carried out with n-hexane in the same ratio;

(g) vacuum-concentrating the aqueous solution until reaching a volume of 70% of the aqueous solution before vacuum-concentration;

(h) filtering the solution to obtain a filtrate and a protein precipitate and adding 96° ethyl alcohol for deproteinization to the filtrate until an alcohol concentration of 50% is reached;

(i) maintaining the aqueous alcoholic solution formed in step (h) at 0 to 5 degrees centigrade for 12 hours, then filtering the aqueous alcohol solution and concentrating the aqueous solution to remove the alcohol until reaching a volume of 70% as against the solution subject to deproteinization;

(j) gradient-treating the protein precipitate formed during step (h) with ammonium sulfate to obtain a low molecular weight fraction of the protein precipitate and combining the low molecular weight protein precipitate with the aqueous solution concentrated during step (i);

(k) removing any histaminic impurities from the combined low molecular weight protein precipitate and aqueous solution by successive treatment with trisodium phosphate, calcium chloride and sodium hydroxide until reaching a pH of 8.5, filtering the combined protein precipitate and aqueous solution, and passing the filtrate through a cationic exchanger column adjusting the pH of the resulting final solution to 4 to 6 to obtain the bioactive concentrate; and (l) adding chondroitin sulfate in an amount of 1% to 3% per 7% to 9% of the antihyaluronidase and anti-inflammatory mucopolysaccharide polymer.

2. The bioactive concentrate defined in claim 1 wherein according to step (a) the raw organic material is in a fresh, frozen or preserved state and is chopped before using.

3. The bioactive concentrate defined in claim 1 wherein according to step (k) the filtrate is passed through the cationic exchanger column at a flow rate such that the pH value of the resulting final solution remains at 4 to 6.

4. The bioactive concentrate defined in claim 1 in a lyophilized state comprising a minimum of 93% active principle consisting essentially of 65 to 84% of the mucopolysaccharide polymer and 9 to 28% of the chondroitin sulfate prepared by lyophilizing the filtrate obtained according to step (k).

5. A process for preparing a bioactive concentrate in a 10% aqueous solution comprising as active principle 7% to 9% of an anti-hyaluronidase and anti-inflammatory mucopolysaccharide polymer and 1% to 3% of chondroitin sulfate, all of these being the active principle having a yellow to light brown color, a pH value ranging from 4 to 6, and an antihyaluronidase activity ranging between 450 and 750 I.U./ml, which comprises the following steps:

(a) extracting at a temperature of 0 to 4 degrees centigrade an organic raw material selected from the group consisting of bovine or sheep cartilaginous connective tissue, umbilical cord, young animal tendons, bowels, and testicles, and sea animals with an aqueous acid solution that contains 0.5% phenol and which has a pH of 2 to 4, in a first phase in a ratio of 1:3.5 to 4 of raw organic material to aqueous acid solution to obtain a first extract and in a second phase in a ratio of 1:1.5 of raw organic material to aqueous acid solution to obtain a second extract, said first phase and said second phase each taking place for 24 hours, stirring for 30 minutes every 3 hours;

(b) combining the first extract and the second extract to obtain a combined aqueous extract;

(c) adjusting the pH of the combined aqueous extract to 4.5 to 5 with calcium hydroxide solution, being then allowed to settle for 8 hours at a temperature of 0 to 4 degrees centigrade;

(d) filtering the combined aqueous extract and concentrating the filtrate by vacuum evaporation at an internal temperature of up to 45 degrees centigrade until reaching a rate of concentration of 7:1;

(e) passing the combined aqueous extract concentrated during step (d) through an anion exchanger column to obtain an aqueous solution;

(f) removing lipids from the aqueous solution by solvent extraction in a ratio of 1:4 solution to extraction solvent in 6 to 10 cycles until the lipids remaining in the aqueous solution do not exceed 1% to 5%, the last defatting cycle is carried out with n-hexane in the same ratio;

(g) vacuum-concentrating the aqueous solution until reaching a volume of 70% of the aqueous solution before vacuum-concentration;

(h) filtering the solution to obtain a filtrate and a protein precipitate and adding 96° ethyl alcohol for deproteinization to the filtrate until an alcohol concentration of 50% is reached;

(i) maintaining the aqueous alcoholic solution formed in step (h) at 0 to 5 degrees centigrade for 12 hours, then filtering the aqueous alcohol solution and concentrating the aqueous solution to remove the alcohol until reaching a volume of 70% as against the solution subject to deproteinization;

(j) gradient-treating the protein precipitate formed during step (h) with ammonium sulfate to obtain a low molecular weight fraction of the protein precipitate and combining the low molecular weight protein precipitate with the aqueous solution concentrated during step (i);

(k) removing any histaminic impurities from the combined low molecular weight protein precipitate and aqueous solution by successive treatment with trisodium phosphate, calcium chloride and sodium hydroxide until reaching a pH of 8.5, filtering the combined protein precipitate and aqueous solution, and passing the filtrate through a cationic exchanger column adjusting the pH of the resulting final solution to 4 to 6; and (l) adding chondroitin sulfate in an amount of 1% to 3% per 7% to 9% of the antihyaluronidase and anti-inflammatory mucopolysaccharide polymer.

6. The process for preparing a bioactive concentrate defined in claim 5 wherein according to step (a) the raw organic material is in a fresh, frozen or preserved state and is chopped before using.

7. The process for preparing a bioactive concentrate defined in claim 5 wherein according to step (k) the filtrate is passed through the cationic exchanger column at a flow rate such that the pH value of the resulting final solution remains at 4 to 6.

8. A pharmaceutical composition having anti-hyaluronidase activity which comprises a therapeutically effective amount of the bioactive concentrate defined in claim 1 in combination with a synergistic substance in a pharmaceutically acceptable inert carrier.

9. The pharmaceutical composition having anti-hyaluronidase activity defined in claim 8 wherein the synergistic substance is a compound selected from the group consisting of heparin, ascorbic acid, sodium acetylsalicylate, lysine acetylsalicylate, Vitamin E, benzyl alcohol, propylene glycol, and I-structured water.

10. The pharmaceutical composition having anti-hyaluronidase activity defined in claim 9 in injectable form.

11. The pharmaceutical composition having anti-hyaluronidase activity defined in claim 9 in the form of an ointment, gel or suppository.

12. The pharmaceutical composition having anti-hyaluronidase activity defined in claim 8 for intramuscular administration in that 1 ml of the aqueous solution contains 0.1 ml of the 10% bioactive concentrate solution, maximum 5 mg of phenol and maximum 2 mg of sodium metabisulfite and has a pH of 4 to 6 and an antihyaluronidase activity of a minimum of 45 I.U./ml.

13. The pharmaceutical composition having anti-hyaluronidase activity defined in claim 4 for intramuscular administration in that 1 ml of an aqueous solution contains 11 mg of the lyophilized bioactive concentrate, maximum 5 mg of phenol and maximum 2 mg of sodium metabisulfite and has a pH of 4 to 6 and an antihyaluronidase activity of a minimum of 45 I.U./ml.

14. The pharmaceutical composition having anti-hyaluronidase activity defined in claim 8 for intraarticular administration in that 1 ml of an aqueous solution contains 15 mg/ml of a dry active substance consisting of the 10% bioactive concentrate solution, 10 mg of sodium acetylsalicylate or lysine acetylsalicylate, 2 mg of ascorbic acid, 0.2 mg of heparin, 20 mg of benzyl alcohol, 40 mg of propylene glycol, and has a pH of 4 to 6, an anti-hyaluronidase activity of a minimum of 65 I.U., a maximum of 2 mg sodium metabisulfite and a maximum of 5 mg of phenol.

15. The pharmaceutical composition having anti-hyaluronidase activity defined in claim 4 for intraarticular administration in that 1 ml of an aqueous solution contains 16.5 mg of the lyophilized bioactive concentrate, 10 mg of sodium acetylsalicylate or lysine acetylsalicylate, 2 mg of ascorbic acid, 0.2 mg of heparin, 20 mg of benzyl alcohol, 40 mg of propylene glycol, and has a pH of 4 to 6, an anti-hyaluronidase activity of a minimum of 65 I.U., a maximum of 2 mg sodium metabisulfite and a maximum of 5 mg of phenol.

16. The pharmaceutical composition having anti-hyaluronidase activity defined in claim 8 as an ointment, gel or suppository, in that 100 g of the composition includes 3 to 10 g of dry active substance consisting of 10% bioactive concentrate solution, 0.3 to 0.5 g of sodium or lysine acetylsalicylate, 0.4 to 0.8 g of ascorbic acid, 0.2 to 0.4 g of Vitamin E, 0.2 g of heparin, 2 to 5 g of a whole plant extract selected from, the group consisting of *Achillea millefolium, Calendula officinalis, Matricaria chamomilla*, Plantago sp., and *Hypericum perforatum*, emulsified in a base of cream or gel containing 40 to 75% I structured water.

17. The pharmaceutical composition having anti-hyaluronidase activity defined in claim 4 as an ointment, gel or suppository, in that 100 g of the composition includes 4 to 12 g of lyophilized bioactive concentrate solution, 0.3 to 0.5 g of sodium or lysine acetylsalicylate, 0.4 to 0.8 g of ascorbic acid, 0.2 to 0.4 g of Vitamin E, 0.2 g of heparin, 2 to 5 g of a whole plant extract selected from, the group consisting of *Achillea millefolium, Calendula officinalis, Matricaria chamomilla*, Plantago sp., and *Hypericum perforatum*, emulsified in a base of cream or gel containing 40 to 75% I structured water.

18. The pharmaceutical composition having anti-hyaluronidase activity defined in claim 17 wherein the I structured water has an increased energy potential and a high transmembrane penetrating capacity.

* * * * *